United States Patent [19]

Saltzman

[11] 3,969,503

[45] July 13, 1976

[54] COMPOSITIONS AND METHODS USEFUL IN RENDERING LITHOGENIC MAMMALIAN BILE NON-LITHOGENIC

[75] Inventor: William H. Saltzman, New Rochelle, N.Y.

[73] Assignee: Intellectual Property Development Corporation, New Rochelle, N.Y.

[22] Filed: Oct. 2, 1975

[21] Appl. No.: 618,900

[52] U.S. Cl. ............................. 424/240; 260/397.1; 424/239
[51] Int. Cl.² ......................................... A61K 31/56
[58] Field of Search .................. 260/397.1; 424/239, 424/240

[56] References Cited
UNITED STATES PATENTS 3,891,681  6/1975  Saltzman .......................... 260/397.1
3,919,266  11/1975  Saltzman .......................... 260/397.1

Primary Examiner—Elbert L. Roberts

[57] ABSTRACT

A method of rendering mammalian bile non-lithogenic which comprises administering to a mammal having lithogenic bile, a small but effective amount of a compound of the formula

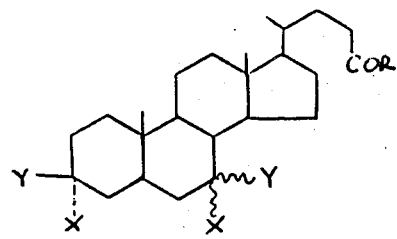

wherein each Y is hydrogen; each X is selected from the group consisting of hydroxy and acyloxy; and when taken together X and Y is oxo (O=); and R is hydroxy, acyloxy or alkoxy; and the pharmaceutically acceptable non-toxic salts thereof; in combination with a small but effective amount of a choloretic agent selected from the group consisting of dehydrocholic acid, glycocholic acid, florantyrone, and tocamphyl.

6 Claims, No Drawings

COMPOSITIONS AND METHODS USEFUL IN RENDERING LITHOGENIC MAMMALIAN BILE NON-LITHOGENIC

This invention relates to a method of rendering lithogenic mammalian bile non-lithogenic. Lithogenic bile is that bile which is super saturated with cholesterol and other lipids and which is a precursor of such disease conditions as cholelithiasis in man. By rendering the lithogenic bile non-lithogenic, it is possible to prevent and even reverse the pathogenic process of cholelithiasis.

It has now been found possible to render lithogenic bile non-lithogenic by the administration to the patient having lithogenic bile of a small but effective amount of a compound of the formula

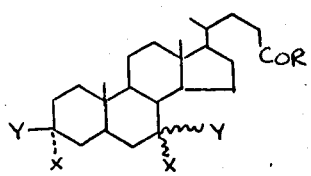

wherein each Y is hydrogen; each X may be hydroxy or acyloxy; and when taken together X and Y is oxo (O=); and R may be hydroxy, acyloxy or alkoxy and the non-toxic pharmaceutically acceptable salts thereof; in combination with a small but effective amount of a choloretic agent selected from the group consisting of dehydrocholic acid, glycocholic acid, florantyrone and tocamphyl.

Preferably, in the practice of this invention, each Y is hydrogen; each X is hydroxy or acyloxy; R is hydroxy; and the choloretic agent may be florantyrone and tocamphyl. Most preferably, Y is hydrogen, X is hydroxy, R is hydroxy and the choloretic agent is florantyrone.

(In this Application and the Claims thereof whenever in the structural formulae a curved line ( $\}$ ) is employed in the connection of atoms it is meant to denote that the connected moiety may be in the $\alpha$- or $\beta$- position as the case may be.)

As employed herein the term "acyloxy" is derived from hydrocarbon carboxylic acids of up to 12 carbon atoms, for example alkanoic acids alkenoic acids, monocyclic aryl carboxylic acids and the like.

Most preferably, the compounds of this invention are administered to the patient perorally in a dosage form which is well suited for this purpose and well known to the skilled worker, for example in capsule, tablet or liquid dosage form. For this purpose, the acceptable and recognized pharmaceutically acceptable inert carriers may be employed in the preparation of the final dosage forms.

For the satisfactory practice of this invention from about 50 to 1500 mg per day of the choloretic agent may be administered to the patient. The compounds of this invention may be administered concurrently, in one composition, or sequentially depending upon the requirements of the patient and the desires of the skilled practitioner.

Among the preferred cholanic acid derivatives which may be employed in this invention are included chenodeoxycholic acid and ursodeoxycholic acid, although the other derivatives may also provide acceptable results.

The pharmaceutically acceptable non-toxic salts of the cholanic acid derivatives may be the alkaline metal salts, such as the sodium or potassium salts, which are well known in the art.

The invention may be further illustrated by the following examples:

EXAMPLE 1

To patients having lithogenic bile are orally administered over a period of seven days the following combinations:

| | Ingredient | Amount/Day |
|---|---|---|
| 1. | Chenodeoxycholic Acid | 250 mg |
| | Florantyrone | 100 mg |
| 2. | Ursodeoxycholic Acid | 250 mg |
| | Tocamphyl | 150 mg |
| 3. | Chenodeoxycholic Acid | 250 mg |
| | Florantyrone | 250 mg |

After treatment, the patients' bile became non-lithogenic.

The invention may be variously otherwise embodied within the scope of the appended claims.

What is claimed is:

1. A composition for rendering lithogenic mammalian bile non-lithogenic which comprises, in combination:

a. a small but effective amount of a compound of the formula

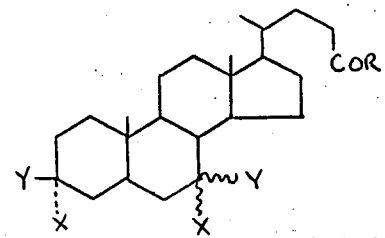

wherein each Y is hydrogen; each X is hydroxy or acyloxy; when taken together X and Y is oxo (O=); and R is hydroxy, acyloxy or alkoxy; and pharmaceutically acceptable salts thereof; and b. a small but effective amount of a choloretic agent selected from the group consisting of dehydrocholic acid, glycocholic acid, florantyrone and tocamphyl.

2. The method of rendering lithogenic mammalian bile non-lithogenic which comprises, administering to a mammal having lithogenic bile, a small but effective amount of a compound of the formula

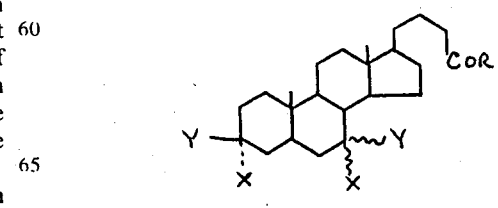

wherein X, Y and R are as defined in claim 1; and a small but effective amount of a choloretic agent selected from the group consisting of dehydrocholic acid, glycocholic acid, florantyrone and tocamphyl.

3. The method of claim 2 wherein the compound is chenodeoxycholic acid or ursodeoxycholic acid.

4. The method of claim 2 wherein the choloretic agent is florantyrone or tocamphyl.

5. The method of claim 2 wherein the compound is chenodeoxycholic acid and the choloretic agent is tocamphyl.

6. The method of claim 2 wherein the compound is chenodeoxycholic acid and the choloretic agent is florantyrone.

* * * * *